US010996228B2

(12) United States Patent
Nagalla et al.

(10) Patent No.: US 10,996,228 B2
(45) Date of Patent: May 4, 2021

(54) BIOMARKERS FOR ASSESSMENT OF PREECLAMPSIA

(71) Applicant: DiabetOmics, LLC, Hillsboro, OR (US)

(72) Inventors: Srinivasa R. Nagalla, Hillsboro, OR (US); Eric S. Bean, Wilsonville, OR (US)

(73) Assignee: DIABETOMICS, INC., Hillsboro, OR (US)

( * ) Notice: Subject to any disclaimer, the term of this patent is extended or adjusted under 35 U.S.C. 154(b) by 173 days.

(21) Appl. No.: 15/833,656

(22) Filed: Dec. 6, 2017

(65) Prior Publication Data
US 2018/0095090 A1   Apr. 5, 2018

Related U.S. Application Data

(62) Division of application No. 14/341,024, filed on Jul. 25, 2014, now abandoned.

(51) Int. Cl.
*G01N 33/68* (2006.01)

(52) U.S. Cl.
CPC ....... *G01N 33/689* (2013.01); *G01N 33/6887* (2013.01); *G01N 2400/02* (2013.01); *G01N 2800/368* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,523,229 A | 6/1996 | Feinberg | |
| 2006/0020043 A1* | 1/2006 | Berlin | A61P 9/00 514/724 |
| 2006/0024725 A1 | 2/2006 | Hussa | |
| 2007/0092911 A1 | 4/2007 | Buechler et al. | |
| 2010/0016173 A1 | 1/2010 | Nagalla et al. | |
| 2011/0280863 A1 | 11/2011 | Buhimchi et al. | |
| 2011/0294227 A1* | 12/2011 | Ahola | G01N 33/689 436/501 |
| 2012/0040356 A1* | 2/2012 | Hussa | B82Y 30/00 435/6.12 |
| 2012/0252015 A1* | 10/2012 | Hindson | C12Q 1/6883 435/6.11 |
| 2013/0274123 A1 | 10/2013 | Nagalla | |
| 2016/0025737 A1 | 1/2016 | Nagalla | |

FOREIGN PATENT DOCUMENTS

| | | |
|---|---|---|
| WO | 2009/097584 A1 | 8/2009 |
| WO | 2016/014832 A1 | 1/2016 |

OTHER PUBLICATIONS

Kupferminc et al., Fetal fibronectin levels are elevated in maternal plasma and amniotic fluid of patients with severe preeclampsia, Am. J. Obstet. Gynecol. 1995 649-653 (Year: 1995).*

Wagner, Diagnosis and Management of Preeclampsia, American Family Physician, 2004, 2317-2324. (Year: 2004).*
Path Organization, "Candidate Blood-Based Biomarkers for Preclampsia Testing", 18 pages, Apr. 2014, https://sites.path.org/mnhtech/assesment/preclampsia-and-eclampsia/biomarkers-blood/.
Petla et al., "Biomarkers for the Management of Preclampsia in Pregnant Women", The Indian Journal of Medical Research, vol. 138, pp. 60-67, 2013.
Rasanen et al., "Marternal Serum Glycosylated Fibronectin as a Point-of-Care Biomarker for Assesment of Preeclampsia", American Journal of Obstetrics and Gynecology, vol. 212. Issue 1, 9 pages, Jan. 2015.
Schneider et al., "Gestational Diabetes and Preeclampsia—Similar Risk Factor Profiles", Early Human Development 88 (2012), pp. 179-184.
De Vivo et al., "Endoglin, PIGF and sFLt-1 as Markers for Predicting Pre-Eclampsia", AOEG, 2008, pp. 837-842.
Rasanen, Juha et al, "Comprehensive Maternal Serum Proteomic Profiles of Predinical and Clinical Preeclampsia," Journal of Proteome Research, Jun. 23, 20-10, vol. 9, pp. 4274-4281.
Kanters, Suzan et al., "Plasma Levels of Cellular Fibronectin in Diabetes," Diabetes Care, Feb. 2001, vol. D, 24, No. 2. pp. 323-327.
Gredmark et al., "Total Fibronectin in Maternal Plasma as a Predictor for Preeclampsia," Gynecologic and Obstetric Investigation, Feb. 1999, vol. 47, No. 2, pp. 89-94.
Rasanen, Juha et al., "Glycosylated Fibronectin as a First-Trimester Biornarker for Prediction of Gestational Diabetes," Obstetrics & Gynecology, Sep. 2013, vol. 122, No. 3, pp. 586-594.
Brubaker, Daniel et al., "The Function of Elevated Plasma Fibronectin in Preeclampsia," American Journal of Obstetrics and Gynecology, Feb. 1992, vol. 166, Issue 2, pp. 526-531.
Rasanen et al. "First-Trimester Maternal Serum Biomarkers for Predication of Gestational Diabetes", American Diabetes Association 72nd Scientific Sessions, Jun. 2012, 2 pages.
International Search Report and Written Opinion for PCT/US2015/041796 dated Sep. 21, 2015; 9 pages.
Kupferminc, et al., "Fetal Fibronectin Levels are Elevated in Maternal Plasma and Amniotic Fluid of Patients with Severe Preeclampsia" Am J Obstet Gynecol 172:649-53 (1995).

* cited by examiner

*Primary Examiner* — Andrea S Grossman
(74) *Attorney, Agent, or Firm* — Schwabe Williamson & Wyatt, PC

(57) ABSTRACT

Disclosed herein are screening tools for fetal/maternal wellness, such as biomarkers for assessing preeclampsia. More specifically, methods are disclosed for assessing the risk of preeclampsia in a subject, the methods including obtaining a first serum sample from the subject, determining a level of glycosylated fibronectin (GlyFn) in the first serum sample, and comparing the determined level of GlyFn with a control value, wherein an elevation in the determined level of GlyFn in the first serum sample relative to the control value indicates that the subject is at increased risk of preeclampsia. Also disclosed are methods of determining the risk of preeclampsia in a subject during a first, second, or third trimester, methods of assessing severity and progression of preeclampsia and complications of a risk of low birth weight or HELLP syndrome.

12 Claims, 17 Drawing Sheets

Figure 1A

GlyFn Serum Biomarker Concentration Within the Longitudinal Cohort by Preeclampsia Status and Trimester

| Biomarker Concentrations | First Trimester | | | Second Trimester | | |
|---|---|---|---|---|---|---|
| | Normotensive Cohort (n=24) | Longitudinal Preeclampsia Cohort (n=11) | Group Difference P* | Normotensive Cohort (n=28) | Longitudinal Preeclampsia Cohort (n=12) | Group Difference P* |
| Gestational age at sample collection (wk) | 9.7 (6.4 – 13.0) | 9.3 (7.3 – 11.0) | 0.79 | 23.3 (17.4 – 26.6) | 22.4 (21.6 – 26.3) | 0.17 |
| GlyFn (µg/ml) | 62 (7 – 198) | 184 (30 – 387) | <0.01 | 41 (9 – 144) | 161 (6 – 848) | <0.01 |

Data are medians (range). *Group differences were determined using Wilcoxon non-parametric t-tests.

Figure 1B

Total Fibronectin Serum Biomarker Concentration Within the Longitudinal Cohort by Preeclampsia Status and Trimester

| Biomarker Concentrations | First Trimester | | | Second Trimester | | |
|---|---|---|---|---|---|---|
| | Normotensive Cohort (n=17) | Longitudinal Preeclampsia Cohort (n=4) | Group Difference P* | Normotensive Cohort (n=20) | Longitudinal Preeclampsia Cohort (n=12) | Group Difference P* |
| Gestational age at sample collection (wk) | 9.6 (6.4 – 10.6) | 10.2 (7.3 – 11.0) | 0.37 | 23.7 (17.4 – 26.6) | 22.6 (21.6 – 26.3) | 0.32 |
| Serum Fibronectin | 54,866 (4,291 – 238,067) | 81,063 (2,761 – 138,945) | 0.93 | 19,411 (2,150 – 292,968) | 20,682 (4,165 – 86,055) | 0.94 |

Data are medians (range). *Group differences were determined using Wilcoxon non-parametric t-tests.

Figure 1C

Average Weekly Change in GlyFn Concentration by Week and Preeclampsia Status Across All Cohorts

| Preeclampsia Status | Number of Subjects (Number of Total Measurements) | Gestational Week | Weekly Change GlyFn (µg/ml) |
| --- | --- | --- | --- |
| Mild Preeclampsia | 5 (10) | 33 to 38 weeks | 81.7 ± 94.1 |
| Severe Preeclampsia | 4 (8) | 33 to 38 weeks | 195.2 ± 88.2 |

Weekly change was determined via linear regression with repeated measurements, using repeated measures for each subject that occurred within two weeks. Data are average change ± standard error.

Figure 1D

Average Weekly Change in Total Serum Fibronectin Concentration by Week and Preeclampsia Status Across All Cohorts

| Preeclampsia Status | Number of Subjects (Number of Total Measurements) | Gestational Week | Weekly Change Fibro |
|---|---|---|---|
| Mild Preeclampsia | 6 (12) | 33 to 38 weeks | 273,434 ±398,205 |
| Severe Preeclampsia | 5 (10) | 33 to 38 weeks | 166,808 ± 258,670 |

Weekly change was determined via linear regression with repeated measurements. Data are average change ± standard error.

Figure 2

Maternal characteristics by preeclampsia status and cohort

| Clinical Characteristics | Normotensive (n=45) | Longitudinal Preeclampsia (n=15) | Clinical Preeclampsia (n=47) | Group Difference P* |
|---|---|---|---|---|
| Maternal age (y)† | 26.5 (19.0 – 35.0) | 28.0 (21.0 – 34.0) | 29.0 (20.0 – 40.0) | 0.14 |
| Gestational age at delivery (wk)† | 40.1 (38.4 – 42.0) | 40.2 (36.7 – 42.0) | 36.3 (21.7 – 40.6) | <0.01 |
| Gestational age at diagnosis of preeclampsia (wk)† | NA | 38.9 (32.0 – 40.0) | 32.7 (21.0 – 37.3) | <0.01 |
| Neonatal birth weight (g)† | 3510 (2690 – 4488) | 3260 (2520 – 4100) | 2250 (315 – 4200) | <0.01 |
| Nulliparity, n (%)† | 29 (83%) | 11 (73%) | 32 (68%) | 0.31 |

Data are medians (range) or n (%). *Group differences were determined using Kruskal-Wallis non-parametric ANOVA for continuous variables and a Fisher's exact tests for the categorical variable. †Maternal age, gestational age at delivery, birth weight, and parity data were unavailable for 13, 12, 12, and 10 normotensive patients, 2, 1, 1, and 0 longitudinal preeclampsia participants. Gestational age at preeclampsia diagnosis was unknown for 8 clinical preeclampsia participants and birth weight was unknown for 1 clinical preeclampsia participant.

Figure 4A

Serum biomarker concentration within the Longitudinal Cohort by preeclampsia status and trimester

| Biomarker Concentrations | First Trimester | | | Second Trimester | | | Third Trimester | | |
|---|---|---|---|---|---|---|---|---|---|
| | Normotensive Cohort (n=24) | Longitudinal Preeclampsia Cohort (n=11) | Group Difference P* | Normotensive Cohort (n=28) | Longitudinal Preeclampsia Cohort (n=12) | Group Difference P* | Normotensive Cohort (n=34) | Longitudinal Preeclampsia Cohort (n=13) | Group Difference P* |
| Gestational age at sample collection (wk) | 9.7 (6.4 – 13.0) | 9.3 (7.3 – 11.0) | 0.79 | 23.3 (17.4 – 26.6) | 22.4 (21.6 – 26.3) | 0.17 | 35.4 (27.0 – 39.7) | 36.4 (28.1 – 38.7) | 0.13 |
| GlyFn (µg/ml) | 62 (7 – 198) | 184 (30 – 387) | <0.01 | 41 (9 – 144) | 161 (6 – 848) | <0.01 | 54 (1 – 199) | 239 (111 – 522) | <0.01 |

Data are medians (range). *Group differences were determined using Wilcoxon non-parametric t-tests.

Figure 5A

Serum biomarker concentrations in the normotensive and clinical preeclampsia cohorts

| Biomarker Concentrations | Normotensive Cohort (n=34) | Third Trimester Clinical Preeclampsia Cohort (n=44) | Group Difference P* |
|---|---|---|---|
| Gestational age at sample collection (wk) | 34.8 (27.0 – 39.0) | 35.0 (27.0 – 39.0) | 0.21 |
| GlyFn (µg/ml) | 55 (1 – 199) | 517 (151 - 1703) | <0.01 |
| sFlt1 | 6.1 (0 – 15.6) | 23.2 (0 – 71.4) | <0.01 |
| PlGF | 361.7 (115.3 – 673.7) | 105.6 (14.6 – 260) | <0.01 |
| sFlt1/PlGF | 0.021 (0.000 – 0.066) | 0.208 (0.061 – 2.781) | <0.01 |

Data are medians (range). Group differences were determined using Wilcoxon non-parametric t-test. Due to insufficient sample volume, data is missing for 7, 22, and 22 normotensive patients and 1, 14, and 14 clinical preeclampsia patients for Flt1, PlGF and Flt1/PlGF ratio, respectively.

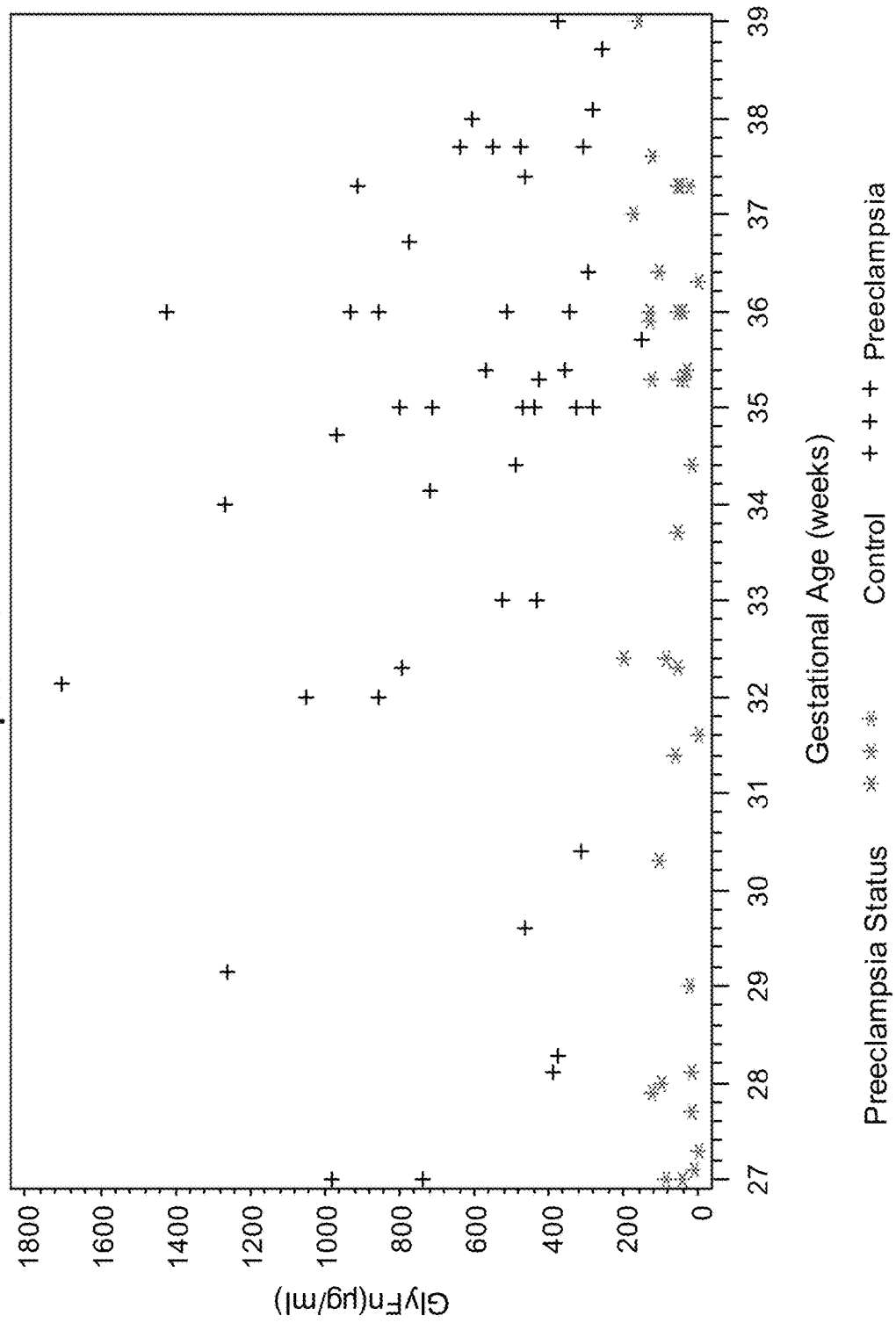

Figure 6A

Average weekly change in GlyFn concentration by week and preeclampsia status

| Preeclampsia Status | Gestational Week | Weekly Change GlyFn (µg/ml) |
|---|---|---|
| Normotensive | 7 to 40 weeks | 0.1 ± 0.6 |
| Mild Preeclampsia | 33 to 38 weeks | 81.7 ± 94.1 |
| Severe Preeclampsia | 33 to 38 weeks | 195.2 ± 88.2 |

Weekly change was determined via mixed models for repeated measurements, using repeated measures for each subject. Data are average change ± standard error.

Receiver operating characteristic curves showing third-trimester preeclampsia classification performance of biomarkers within all cohorts

Figure 7

Third-trimester preeclampsia classification performance of biomarkers within all cohorts

| Biomarker | AUROC (95% CI) | P-value for comparison to GlyFn ROC |
|---|---|---|
| GlyFn (µg/ml) | 0.99 (0.98 – 1.00) | NA |
| sFlt1 | 0.96 (0.89 – 1.00) | 0.11 |
| PlGF | 0.94 (0.86 – 1.00) | 0.10 |
| Flt1/PlGF | 0.98 (0.94 – 1.00) | 0.29 |

AUROC, area under the receiver operating characteristic curve; CI, confidence interval.

Figure 8

GlyFn POC values for prediction of preeclampsia at varying prevalence estimates

| Threshold of GlyFn POC | Sensitivity and Specificity | Predictive Value | Predictive Value (95% CI) with Varying Prevalence Estimates | | |
|---|---|---|---|---|---|
| | | | 3% | 5% | 7% |
| 176.4 | Sensitivity: 0.97 | Positive Predictive Value | 0.41 (0.19 – 0.67) | 0.47 (0.23 – 0.72) | 0.50 (0.26 – 0.75) |
| | Specificity: 0.93 | Negative Predictive Value | 0.95 (0.83 – 0.99) | 0.94 (0.80 – 0.98) | 0.93 (0.77 – 0.98) |

AUROC, area under the receiver operating characteristic curve; CI, confidence interval.

Figure 9

Relationship of third-trimester GlyFn levels to clinical characteristics and outcomes in normotensives and clinical preeclampsia

| Clinical Characteristic or Outcome | Pearson Correlation Coefficient | Change in Outcome for Every 100 μg change in GlyFn* | P-value* |
|---|---|---|---|
| Gestational Age at Delivery† | -0.59 | -0.49 weeks | <0.01 |
| Birth Weight† | -0.57 | -129.4 g | <0.01 |
| Systolic Blood Pressure† | 0.27 | +1.39 mmHg | 0.04 |
| Diastolic Blood Pressure† | 0.34 | +1.14 mmHg | 0.01 |
| Gestational Age of Diagnosis of Preeclampsia† | -0.17 | | 0.27 |
| Uric Acid† | 0.52 | +13.6 mmol/L | <0.01 |
| ALAT†† | 0.42 | +5.88 U/L | <0.01 |
| Proteinuria†† | -0.07 | | 0.68 |

*Change in outcome was determined via linear regression slope and p-value was calculated based on this slope. †Blood pressure, gestational age of delivery and birth weight data were unavailable for 35, 7, and 7 normotensive participants. ††Gestational age of diagnosis of preeclampsia, uric acid, ALAT, and proteinuria values were only collected from preeclampsia participants and were missing for 6, 2, and 9 clinical preeclampsia patients.

BIOMARKERS FOR ASSESSMENT OF PREECLAMPSIA

CROSS REFERENCE TO RELATED APPLICATION

The present application is a divisional of U.S. application Ser. No. 14/341,024, filed Jul. 25, 2014, entitled "BIOMARKERS FOR ASSESSMENT OF PREECLAMPSIA," the disclosure of which is hereby incorporated by reference in its entirety.

TECHNICAL FIELD

Embodiments herein relate to the field of screening tools for fetal/maternal wellness, and, more specifically, to biomarkers for the assessment of preeclampsia.

BACKGROUND

Preeclampsia is a potentially life-threatening complication unique to pregnancy, and it occurs in up to 7% of all pregnancies. Hypertensive disorders, including preeclampsia, are the second leading cause of maternal mortality worldwide, and are responsible for 10%-25% of all maternal deaths. Unfortunately, clinical manifestations of preeclampsia may occur late in the course of the disease, and may be associated with adverse maternal and neonatal outcomes. Robust biomarkers for screening, diagnosis, and monitoring, particularly with respect to severe preeclampsia, are necessary to appropriately manage preeclampsia and to mitigate adverse outcomes. This is particularly the case in developing countries, where the burden of disease is greatest, and where medical intervention is often ineffective due to late presentation. Furthermore, the incidence of preeclampsia has been increasing since 1990, which may be directly related to the increase in obesity. Early and robust diagnostic tests are urgently needed in order to provide for appropriate triage to skilled medical facilities and management of preeclamptics.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIGS. 1A-1D are tables showing GlyFn serum biomarker concentration within a longitudinal cohort by preeclampsia status and trimester (FIG. 1A), total fibronectin serum biomarker concentration within the longitudinal cohort by preeclampsia status and trimester (FIG. 1B), the average weekly change in GlyFn concentration by week and preeclampsia status across all cohorts (FIG. 1C), and the average weekly change in total serum fibronectin concentration by week and preeclampsia status across all cohorts (FIG. 1D), in accordance with various embodiments;

FIG. 2 is a table showing maternal characteristics by preeclampsia status and cohort, in accordance with various embodiments;

FIGS. 4A and 4B are a table showing serum biomarker concentration within the longitudinal cohort by preeclampsia status and trimester (FIG. 4A), and a plot of GlyFn concentration across the span of pregnancy in the longitudinal cohort (FIG. 4B), in accordance with various embodiments;

FIGS. 5A and 5B are a table showing serum biomarker concentrations in the normotensive and clinical preeclampsia cohorts (FIG. 5A), and a plot of $2^{nd}$ and $3^{rd}$ trimester GlyFn concentration in normotensive controls and clinical preeclampsia patients (FIG. 5B), in accordance with various embodiments;

FIGS. 6A and 6B are a table showing average weekly change in GlyFn concentration by week and preeclampsia status (FIG. 6A), and a receiver operating characteristic curves showing third-trimester preeclampsia classification performance of biomarkers within all cohorts (FIG. 6B), in accordance with various embodiments;

FIG. 7 is a table showing third-trimester preeclampsia classification performance of biomarkers within all cohorts, in accordance with various embodiments;

FIG. 8 is a table showing GlyFn POC values for prediction of preeclampsia at varying prevalence estimates, in accordance with various embodiments;

FIG. 9 is a table showing a relationship of third-trimester GlyFn levels to clinical characteristics and outcomes in normotensives and clinical preeclampsia, in accordance with various embodiments.

DETAILED DESCRIPTION OF DISCLOSED EMBODIMENTS

Figure 3:
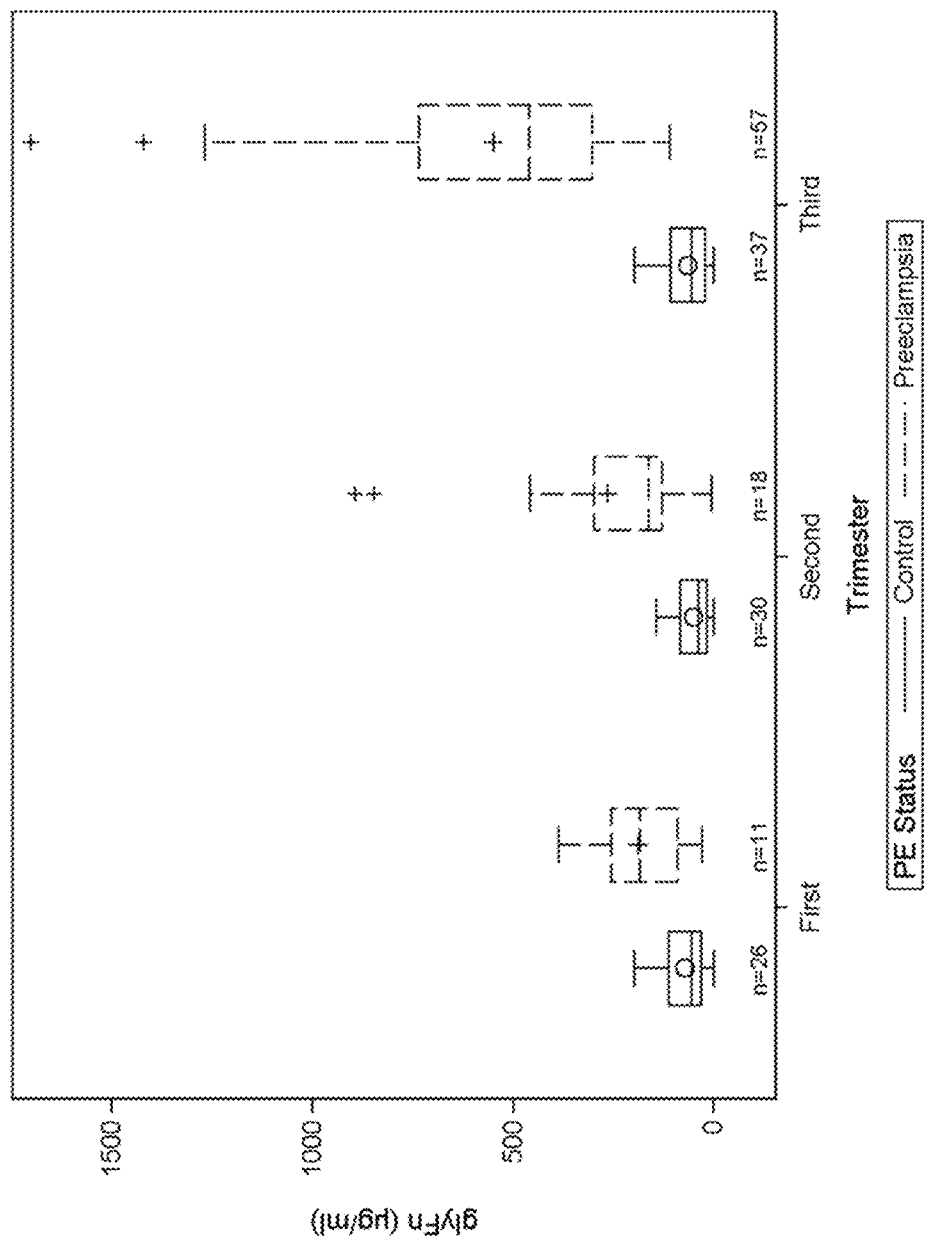
FIG. 3 is a graph illustrating that GlyFn levels were significantly higher in patients with preeclampsia across 1st, 2nd and 3rd trimesters, where GlyFn levels were measured in serum from 45 normotensive control (circles and solid lines) and 62 preeclampsia (pluses and dotted lines) subjects across first, second, and third trimesters, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Disclosed herein in various embodiments are methods for assessing the risk of, predicting, diagnosing, and monitoring preeclampsia in a subject. Methods disclosed herein also may be used for distinguishing between mild preeclampsia and severe preeclampsia. Also disclosed are methods of predicting or diagnosing low birth weight and/or HELLP syndrome, a life-threatening complication of preeclampsia involving hemolysis, elevated liver enzymes, and low platelet count. In various embodiments, the methods may include measuring the level of glycosylated fibronectin (GlyFn) in a biological sample from a subject, such as a serum sample. Although serum samples are described herein, one of skill in the art will appreciate that the disclosed methods may be adapted for use with other biological samples, such as whole blood, plasma, urine, saliva, or other bodily fluids.

Fibronectin (Fn) is an abundant protein with a wide spectrum of functions. An exemplary GENBANK® Accession number for human fibronectin is Genbank Accession No. P02751. As a result of alternative splicing and proteolysis, the Fn gene encodes a collection of isoforms that differ in sequence and length. The majority of the Fn present in serum or plasma is termed plasma Fn (pFn), which is produced and secreted in a soluble form by hepatocytes, while so-called cellular Fn (cFn) is produced by numerous cell types, including fibroblasts, endothelial cells, and smooth muscle cells. A major distinction between pFn and cFn is the presence of alternatively spliced extra domains A and B (ECA/B) that are absent in pFn but variably present in cFn. It is increasingly clear that cFn is also found in the circulation, especially in various pathological conditions, including diabetes and inflammation. Both pFn and cFn exhibit complex patterns of glycosylation, and elevated levels of a specific glycosylated version of Fn (Fn-SNA) in maternal serum have been shown to predict gestational diabetes. However, prior to the present disclosure, elevated GlyFn was not known to be associated with preeclampsia.

As shown herein, whereas GlyFn may be used for assessing preeclampsia and related conditions, total fibronectin levels do not correlate with preeclampsia risk. FIGS. 1A-1D are tables showing GlyFn serum biomarker concentration within a longitudinal cohort by preeclampsia status and trimester (FIG. 1A), total fibronectin serum biomarker concentration within the longitudinal cohort by preeclampsia status and trimester (FIG. 1B), the average weekly change in GlyFn concentration by week and preeclampsia status across all cohorts (FIG. 1C), and the average weekly change in total serum fibronectin concentration by week and preeclampsia status across all cohorts (FIG. 1D), in accordance with various embodiments. Thus, total fibronectin levels (FIG. 1B) and rate of change in total fibronecting levels (FIG. 1D) are not predictive of preeclampsia status. By contrast, as discussed in greater detail below, both the level of GlyFn (FIG. 1A) and the rate of change per week of pregnancy in the level of GlyFn (FIG. 1C) may be used to assess the risk of, predict, and/or diagnose preeclampsia and associated conditions.

In various embodiments, the disclosed methods include obtaining a biological sample, such as a serum sample, whole blood sample, plasma sample, or saliva sample, from a pregnant subject. The level of glycosylated fibronectin (GlyFn) in the sample is then determined using any of several possible methods, and the level of GlyFn in the sample is compared to a control value, such as a reference value representative of a GlyFn level normally found in a subject who will not go on to develop preeclampsia. In various embodiments, if the level of GlyFn in the sample is determined to be similar to the control value (for example, when there is no statistically significant difference between the sample GlyFn value and the reference value, or when the sample GlyFn value is determined to be within a range defined as "normal") then the subject may be categorized as not having preeclampsia or being at low risk of developing preeclampsia. However, when the sample GlyFn value is determined to be elevated relative to the control value (e.g., elevated to a statistically significant degree with respect to the control value or outside a predetermined range of "normal" values) then the subject may be determined to have preeclampsia or be at elevated risk of developing preeclampsia.

More specifically, in some embodiments, methods are disclosed for determining the risk of preeclampsia in a subject during the first trimester. In these embodiments, the control value may be a reference value (or a range of "normal" values) representative of a level of GlyFn in a sample from a first trimester subject who will not go on to develop preeclampsia. In some embodiments, an "elevation" in the sample GlyFn level relative to the first trimester control value may be at least a 15% elevation, such as a 20% elevation, a 30% elevation, a 40% elevation, a 50% elevation, a 60% elevation, a 70% elevation, an 80% elevation, a 90% elevation, a 100% elevation, or even more, such as a 125% elevation or a 150% elevation. For instance, a normal (non-preeclamptic) range of GlyFn in a sample from a first trimester subject may range from 10-150 µg/ml, and an abnormal (e.g., preeclamptic) level of GlyFn may be greater than 150 µg/ml, such as about 175 µg/ml or higher.

In other embodiments, the method may be a method of determining the risk of preeclampsia in a subject during the second trimester. In these embodiments, the control value may be a reference value (or range of "normal" reference values) representative of a level of GlyFn in a sample from a second trimester subject who will not go on to develop preeclampsia. In some embodiments, an "elevation" in the sample GlyFn level relative to the second trimester control value may be at least a 15% elevation, such as a 20% elevation, a 30% elevation, a 40% elevation, a 50% elevation, a 60% elevation, a 70% elevation, an 80% elevation, a 90% elevation, a 100% elevation, or even more, such as a 125% elevation or a 150% elevation. For instance, a normal (non-preeclamptic) range of GlyFn in a sample from a second trimester subject may range from 10-150 µg/ml, and an abnormal (e.g., preeclamptic) level of GlyFn may be greater than 150 µg/ml, such as about 175 µg/ml or higher.

In still other embodiments, the method may be a method of determining the risk of preeclampsia in a subject during the third trimester. In these embodiments, the control value may be a reference value (or range of "normal" reference values) representative of a level of GlyFn in a sample from a third trimester subject who will not go on to develop preeclampsia. In some embodiments, an "elevation" in the sample GlyFn level relative to the third trimester control value may be at least a at least a 30% elevation, such as a 40% elevation, a 50% elevation, a 60% elevation, a 70% elevation, a 80% elevation, a 90% elevation, a 100% elevation, a 125% elevation, a 150% elevation, or even more, such as a 200% elevation or a 300% elevation. For instance, a normal (non-preeclamptic) range of GlyFn in a sample from a first trimester subject may range from 10-150 μg/ml, and an abnormal (e.g., preeclamptic) level of GlyFn may be greater than 150 μg/ml, such as about 200 μg/ml or higher.

Still other embodiments may be methods of assessing the risk of low birth weight, methods of assessing the risk of HELLP syndrome, or methods of diagnosing preeclampsia in a subject. For example, in some embodiments, the subject may be in the third trimester of pregnancy, and a level of GlyFn in the serum sample from the subject that is equal to or greater than about 100 μg/ml, such as about 110 μg/ml, about 120 μg/ml, about 130 μg/ml, about 140 μg/ml, about 150 μg/ml, about 160 μg/ml, about 170 μg/ml, about 180 μg/ml, about 200 μg/ml, or even more, may indicate that the subject has preeclampsia. In various embodiments, a level of GlyFn in the serum sample from the subject that is equal to or greater than about about 250 μg/ml, such as about 275 μg/ml, about 300 μg/ml, about 325 μg/ml, about 350 μg/ml, about 375 μg/ml, about 400 μg/ml, about 425 μg/ml, about 450 μg/ml, about 475 μg/ml, about 500 μg/ml, or even more, may indicate that the subject is at risk of having a low birth weight (small for gestational age or SGA) baby or of developing HELLP syndrome. In particular embodiments, a level of GlyFn in the serum sample from the subject that is equal to or greater than about 500 μg/ml or even more may indicate that the subject has a high risk of having a low birth weight (SGA) baby or of developing HELLP syndrome.

Still other embodiments are methods of distinguishing between mild preeclampsia and severe preeclampsia. In these embodiments, the method may further include obtaining at least one additional serum sample from the subject at least one week after the first serum sample was obtained, such as a series of weekly samples between weeks 33-38 of pregnancy. In various embodiments, the method may include determining the level of glycosylated fibronectin (GlyFn) in the second serum sample and comparing the level of GlyFn in the second serum sample with the previously determined level of GlyFn in the first serum sample. In various embodiments, a weekly increase in the level of GlyFn in the second (or subsequent) serum sample compared to the level of GlyFn in the first (or previous) serum sample may indicate that a diagnosis of preeclampsia is warranted. More specifically, a weekly increase of between about 15 μg/ml and 125 μg/ml, such as about 25 μg/ml, about 35 μg/ml, about 45 μg/ml, about 55 μg/ml, about 65 μg/ml, about 75 μg/ml, about 85 μg/ml, about 95 μg/ml, about 105 μg/ml, about 115 μg/ml, or about 125 μg/ml, may indicate that the subject has mild preeclampsia. Likewise, in various embodiments, a weekly increase of more than about 150 μg/ml, such as about 175 μg/ml, about 200 μg/ml, about 225 μg/ml, about 300 μg/ml, about 325 μg/ml, about 350 μg/ml, about 375 μg/ml, about 400 μg/ml, or about 425 μg/ml or more, may indicate that the subject has severe preeclampsia.

Statistical methods for determining if the abundance of a protein of interest is increased or decreased relative to a reference sample are well known in the art, and are described below. In various embodiments, determination of the level of GlyFn in a biological fluid, such as whole blood, plasma, serum, saliva, or urine, may be performed using a variety of methods known to those of skill in the art. In various embodiments, in a direct comparative analysis, the reference sample and test sample may be treated exactly the same way, in order to correctly represent the relative abundance of GlyFn and obtain accurate results.

For example, in various embodiments, the proteins present in the biological samples may be separated by 2D-gel electrophoresis according to their charge and molecular weight. For instance, the proteins may first be separated by their charge using isoelectric focusing (one-dimensional gel electrophoresis), for example using immobilized pH-gradient (IPG) strips, which are commercially available. In various embodiments, the second dimension may be an SDS-PAGE analysis, where the focused IPG strip may be used as the sample. After two-dimensional gel electrophoresis separation, proteins may then be visualized with conventional dyes, such as Coomassie Blue or silver staining, and imaged using known techniques and equipment, such as, for example Bio-Rad GS800 densitometer and PDQUEST™ software.

In some embodiments, individual spots may then be cut from the gel, de-stained, and subjected to tryptic digestion, allowing the peptide mixtures to be analyzed by mass spectrometry (MS). Alternatively, in some embodiments, the peptides may be separated, for example by capillary high pressure liquid chromatography (HPLC) and may be analyzed by MS either individually, or in pools. If desired, in some embodiments, the amino acid sequences of the peptide fragments and the proteins from which they derived may be determined. Although it is possible to identify and sequence all or some of the proteins present in a proteomic profile, this typically is not necessary for the diagnostic use of the methods disclosed herein.

As discussed above, in various embodiments, a diagnosis of or risk of preeclampsia may be based on characteristic similarities or differences between a reference sample and a test sample. For example, in various embodiments, if the proteomic profile is presented in the form of a mass spectrum, the expression signature may be a peak representing GlyFn that differs, qualitatively or quantitatively, from the mass spectrum of a corresponding normal sample. Thus, any statistically significant change in the amplitude or shape of an existing peak may reflect a change in a level of GlyFn relative to a control.

Other embodiments may utilize protein arrays to monitor GlyFn levels, enabling high-throughput analysis. Protein arrays are known to those of skill in the art, and generally are formed by immobilizing proteins, such as antibodies specific for proteins of interest, like GlyFn, on a solid surface, such as glass, silicon, nitrocellulose, or PVDF using any of a variety of covalent and non-covalent attachment chemistries well known in the art. The arrays may be probed with fluorescently labeled proteins from two different sources, such as normal and test samples, and fluorescence intensity may reflect the expression level of a target protein, such as GlyFn.

Various embodiments also may use any of various immunoassay formats for quantification of protein expression levels. In general, immunoassays may be homogeneous or heterogeneous. For instance, in various embodiments, an enzyme-linked immunosorbant assay (ELISA) may be used to quantify protein expression. In one example, in a "sandwich" assay, a solid surface may be coated with a solid phase antibody, and the test sample may be allowed to react with the bound antibody. Any unbound antigen may then be washed away, and a known amount of enzyme-labeled antibody may then be reacted. The label may then be quantified as a direct measurement of the amount of protein of interest present in the sample.

In some embodiments, ELISA may also be used as a competitive assay. For example, in a competitive assay, the test sample containing the protein of interest may be mixed with a precise amount of enzyme-labeled protein of interest, and both may compete for binding to an antibody attached to a solid surface. In various embodiments, excess free enzyme-labeled protein may be washed off before the substrate for the enzyme is added, and the color intensity resulting from the enzyme-substrate interaction may be used as a measure of the amount of protein of interest in the test sample.

Various other embodiments may quantify the proteins of interest using an Enzyme Multiplied Immunoassay Technique (EMIT), which may include a test sample, enzyme-labeled molecules of the proteins of interest, antibodies specific to the proteins of interest, and a specific enzyme chromogenic substrate. In various embodiments, an excess of the specific antibodies may be added to the test sample, and the proteins of interest may then bind to the antibodies. In various embodiments, a measured amount of the corresponding enzyme-labeled proteins may then be added to the mixture, and antibody binding sites not occupied by proteins of interest from the test sample may be occupied with molecules of the enzyme-labeled protein. As a result, in various embodiments, enzyme activity may be reduced because only free enzyme-labeled protein can act on the substrate, and the amount of converted substrate may reflect the amount of free enzyme left in the mixture. In various embodiments, a high concentration of the protein of interest in the sample may result in higher absorbance readings.

Various other embodiments include immunoassay kits for the quantification of the proteins of interest in a test sample. In various embodiments, these kits may include, in separate containers, one or more monoclonal or polyclonal antibodies having binding specificity for GlyFn, and, optionally, anti-antibody immunoglobulins, particularly labeled anti-antibody immunoglobulins.

Also disclosed herein are capture devices and sample collection kits for use in the disclosed methods. In some embodiments, the disclosed methods may be carried out using a sample capture device, such as a lateral flow device (for example a lateral flow test strip) that may allow quantification of GlyFn. Lateral flow devices are available in numerous different configurations, but in one example, a test strip may include a flow path from an upstream sample application area to a test site, such as from a sample application area through a mobilization zone to a capture zone. In various embodiments, the mobilization zone may contain a mobilizable marker that may interact with the protein of interest, and the capture zone may contain a reagent that binds the protein of interest for detection and/or quantification. In other embodiments, exemplary sample collection kits may include an absorbent medium, such as filter paper, that may include indicia for the placement of the test sample on the medium. Such kits also may include a lancing device for obtaining a blood sample from a subject, and optionally, a mailer for sending the test sample to a physician or laboratory for analysis. Such sample collection kits may be used, for example, during standard prenatal exams, such as the eight week, twelve week, sixteen week, twenty week, twenty-four week, twenty-eight week, thirty week, or subsequent-week visit, and/or sample collection may be performed when blood is obtained for other standard prenatal tests.

The following Examples are provided for illustration purposes, and are not to be construed as limiting in any way.

EXAMPLES

Example 1: Subject Selection

Study participants were recruited from two patient populations. A longitudinal cohort consisted of 60 women who were sampled serially throughout pregnancy, with the first sample taken between 6 and 14 weeks of gestation and an additional sample obtained in each trimester. Forty-five women remained normotensive and 15 developed preeclampsia at various gestational ages. A clinical preeclampsia cohort of 47 patients who were diagnosed with preeclampsia at various gestational ages was analyzed to measure the rate of change in GlyFn levels during the course of their preeclampsia. Preeclampsia status was defined having a systolic blood pressure ≥140 mmHg or a diastolic blood pressure ≥90 mmHg with proteinuria ≥300 mg/day. Two hundred and seven serum samples were analyzed using a plate assay, and 86 serum samples were also analyzed using a GlyFn point-of-care (POC) device. Twenty-six participants included in the analysis had one measurement, 62 had two measurements, and 19 had three measurements.

The study participants were recruited from the Department of Obstetrics and Gynecology, Oulu University Hospital, Oulu, Finland, and the Finnish maternity cohort serum bank at the National Institute for Health and Welfare between 2004 and 2006. The research protocol was approved by the Oulu University Hospital Ethics Committee, and all participants provided informed consent.

Example 2: Analyte Assays

Maternal blood was spun, aliquoted, and stored at −80° C. until subjected to the assays described below.

GlyFn plate assay: Reacti-Bind plates (Thermo Scientific, Rockford, Ill.) were coated with an Fc fragment-specific goat anti-mouse IgG (Jackson ImmunoResearch, West Grove, Pa.; cat #115-005-071) in carbonate buffer, pH 9.6, and incubated at 4° C. overnight, followed by washing with PBS-0.05% Tween 20. Plates were blocked with 3% bovine serum albumin in phosphate-buffered saline (PBS), pH 7.2, for one hour at room temperature. Plates were then washed with PBS-0.05% Tween 20 buffer and an anti-GlyFn monoclonal antibody was added and incubated for 45 minutes at room temperature. Although a particular antibody was used in this Example, one of skill in the art will appreciate that any antibody that is specific for glycosylated (but not unglycosylated) fibronectin may be used. Additionally, other specific binding agents, such as lectins, that specifically bind glycosylated (but not unglycosylated) fibronectin, may be used in similar assays for detecting and measuring GlyFn. Generally speaking, antibodies for use in the methods and devices of this disclosure may be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

Samples and standard protein (human Fn isolated from serum, R&D Systems cat #1918-FN-02M) were incubated for 45 minutes, washed, and a biotinylated anti-human Fn polyclonal antibody was added. Labeling was performed using High-Sensitivity Streptavidin-horseradish peroxidase (HRP) (Thermo Scientific; cat #21130). After incubation for 45 minutes followed by washing the plate with PBS-0.05% Tween 20 buffer, the plate was developed with 100 μl of K-Blue TMB Substrate (Neogen, Glasgow; cat #304177) and quenched by the addition of 2N $H_2SO_4$.

GlyFn POC assay: A fluorescence immunoassay, comprising an automated cassette reader (LRE Medical cPoC Reader, LRE Medical, Oceanside, Calif.) and a disposable, single-use, plastic assay cartridge was developed that employs standard immunoassay techniques to specifically and quantitatively detect GlyFn in serum specimens. The polyclonal anti-Fn antibody employed in the plate assay described above was conjugated to a Tide Fluor™ 5WS succinimidyl ester fluorescent tag (AAT Bioquest, Sunnyvale, Calif.; cat #2281) and served as the detection antibody. The monoclonal anti-GlyFn antibody employed in the plate assay described above served as the capture antibody and was immobilized on a solid phase (test zone). Goat polyclonal anti-rabbit IgG, Fc antibody (Jackson ImmunoResearch Laboratories, Inc.; cat #111-045-046) was immobilized in a separate capture zone to act as a reference for the test zone and to provide assurance that the device performed properly.

Serum was diluted in assay buffer and applied to the test strip. The serum flows down the diagnostic lane via capillary action, taking the fluorescent detection antibody into suspension. GlyFn in the specimen binds to the fluorescent antibody to form a multivalent complex that is captured by the antibody immobilized in the test zone. The cartridge is inserted into the cassette reader and quantitative measurements of glyFn concentration in the range from 10 to 2000 µg/mL are displayed on the meter screen and/or printout after 10 minutes.

sFlt1 levels were determined by ELISA. Due to the large amount of serum needed for this assay, 13 participants were unable to be assayed for this analyte. PlGF levels were determined using a commercial kit (R&D Systems Human PIGF Quantikine ELISA Kit; cat #DPG00). Due to inadequate serum sample, this analysis was subset to 57 subjects. Plates were read using an Epoch plate reader (BioTek, Winooski, Vt.) at 450 nm, and data were processed using Gen5 software version 1.10.8 and analyzed as described below.

Example 3: Statistical Analysis

Analyses were performed on the normotensive, longitudinal preeclampsia, and clinical preeclampsia samples separately, and were combined or compared only where indicated. Maternal characteristics were compared across study groups using Kruskal-Wallis non-parametric ANOVA for continuous variables and Fisher's exact test for categorical variables. Comparisons of GlyFn levels between longitudinal participants with and without preeclampsia were performed with parametric and non-parametric Wilcoxon t-tests using the age-matched measures for each subject within a trimester. For analysis of sFlt1, PlGF, and the sFlt1/PlGF ratio, samples were subset to the third trimester and the normotensive group was compared to the clinical preeclampsia cohort via non-parametric Wilcoxon t-tests. To assess the change in GlyFn levels for participants with mild and severe preeclampsia, a subset of patients with two repeated measures between 33 and 38 weeks were used to calculate the average weekly change.

Receiver-operating characteristic (ROC) curves were generated using predicted probabilities from logistic regression models using a single age-matched measure from 14 to 40 weeks of gestation for each subject from all cohorts. The area under the ROC curve (AUROC) and corresponding 95% confidence limits were calculated using simple logistic regression. Sensitivity and specificity were reported based on thresholds chosen, and 95% confidence limits calculated by the score method with a continuity correction are reported. Statistical tests of differences in ROC curves were calculated using contrast matrices of differences. Hypothetical predictive values and 95% confidence intervals (CI) were calculated using the standard logit method using a population prevalence of 3%, 5%, or 7%.

A post-hoc analysis of maternal and fetal clinical characteristics and outcomes versus GlyFn values was performed. Within all cohorts, GlyFn was compared to gestational age at delivery, birth weight, systolic blood pressure, and diastolic blood pressure. Within clinical preeclampsia participants, comparative analyses were performed with GlyFn with respect to gestational age of preeclampsia start, uric acid, ALAT, proteinuria, HELLP syndrome, small-for-gestational age, and placental insufficiency. For continuous variables, Pearson correlation coefficients and linear regression slopes were calculated. For interpretability, linear regression slopes were calculated to reflect a change in GlyFn of 100 µg. For categorical variables, Fisher's exact tests were performed by categorizing participants as those with or without GlyFn levels ≥500 µg.

A comparison of the GlyFn plate assay to the GlyFn POC was performed on samples assayed by both methods to assess the POC test's ability to distinguish between participants with and without preeclampsia as well as to assess the ability of GlyFn to monitor progression of preeclampsia during the second and third trimesters. Correlation coefficients were calculated to compare the two measures. ROC curves were generated separately for GlyFn plate and POC data for classification of control versus PE, control versus mild PE, and mild versus severe PE, and the AUROC for each was compared between glyFn plate and POC assays. Reported P values are two-sided, and P<0.05 was considered statistically significant. Statistical analysis was performed using SAS software, Version 9.3, of the SAS System for Windows.

Example 4: GlyFn for Assessment of Preeclampsia

FIG. 2 is a table showing maternal characteristics by preeclampsia status and cohort, in accordance with various embodiments. Patients in the clinical preeclampsia group were more likely to give birth earlier (p<0.01) and have lower neonatal birth weights (p<0.01; FIG. 2). There was no difference in maternal age (p=0.14) and nulliparity (0.31) between the cohorts. Median gestational age at diagnosis of preeclampsia was significantly later in the longitudinal preeclampsia group than in the clinical preeclampsia cohort.

Figure 4B:
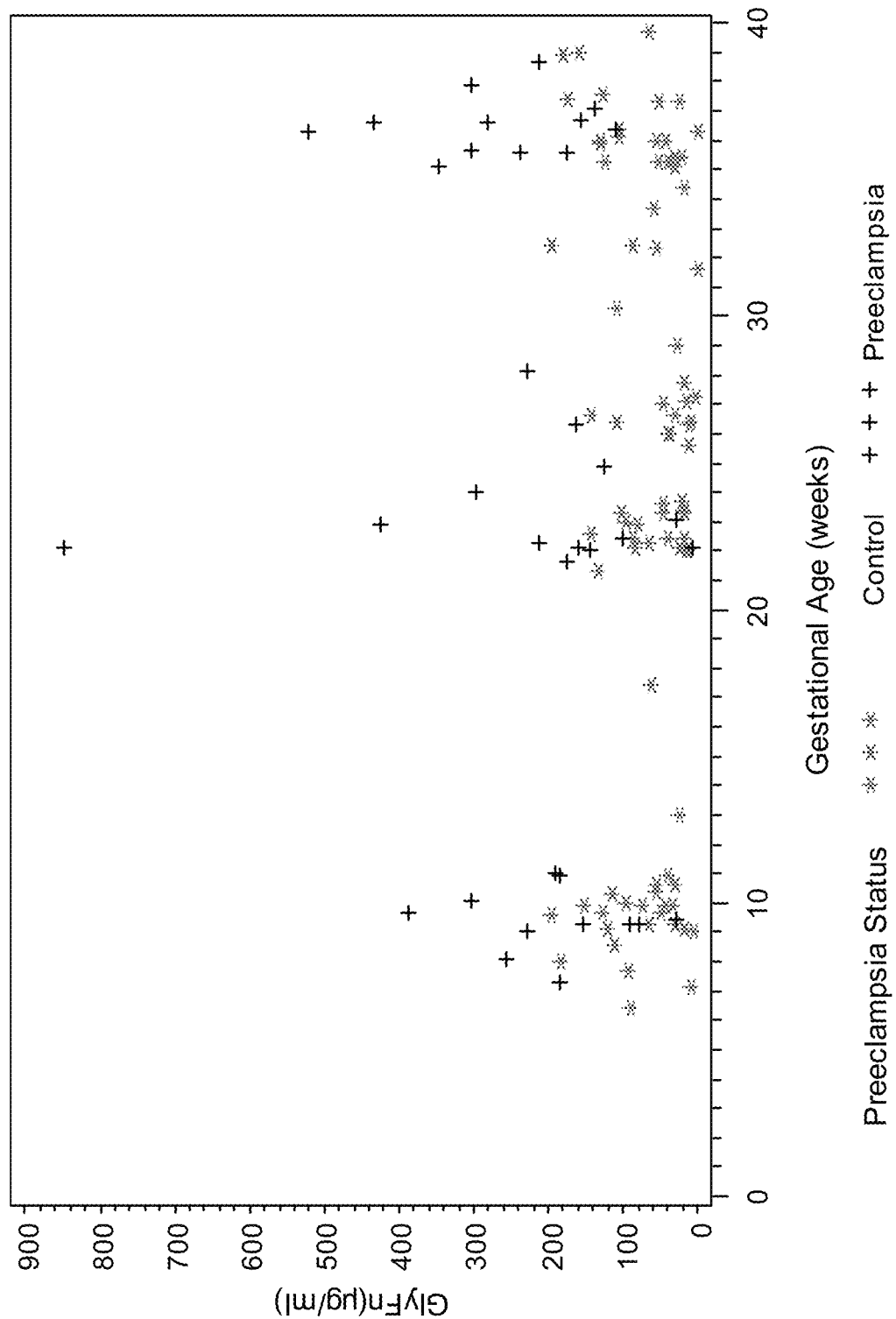

FIG. 3 is a graph illustrating a comparison of the longitudinal normotensive and preeclampsia groups, showing that, within each trimester, GlyFn levels were significantly higher in patients with preeclampsia than in controls, and FIGS. 4A and 4B are a table showing serum biomarker concentration within the longitudinal cohort by preeclampsia status and trimester (FIG. 4A), and a plot of GlyFn concentration across the span of pregnancy in the longitudinal cohort (FIG. 4B), in accordance with various embodiments. A comparison of the longitudinal normotensive and preeclampsia groups found that, within each trimester, GlyFn levels were significantly higher in patients with preeclampsia than in controls (p<0.01, FIGS. 3, 4A and 4B).

FIGS. 5A and 5B are a table showing serum biomarker concentrations in the normotensive and clinical preeclampsia cohorts (FIG. 5A), and a plot of $2^{nd}$ and $3^{rd}$ trimester GlyFn concentration in normotensive controls and clinical preeclampsia patients (FIG. 5B), in accordance with various embodiments. To assess the change in serum biomarkers during the third trimester, levels of GlyFn, sFLt1, PlGF, and the sFLT1/PlGF ratio were compared between age-matched samples from the normotensive control and clinical preeclampsia cohorts. There was a significant difference in all serum biomarkers between participants with and without preeclampsia (p<0.01).

Figure 6B:
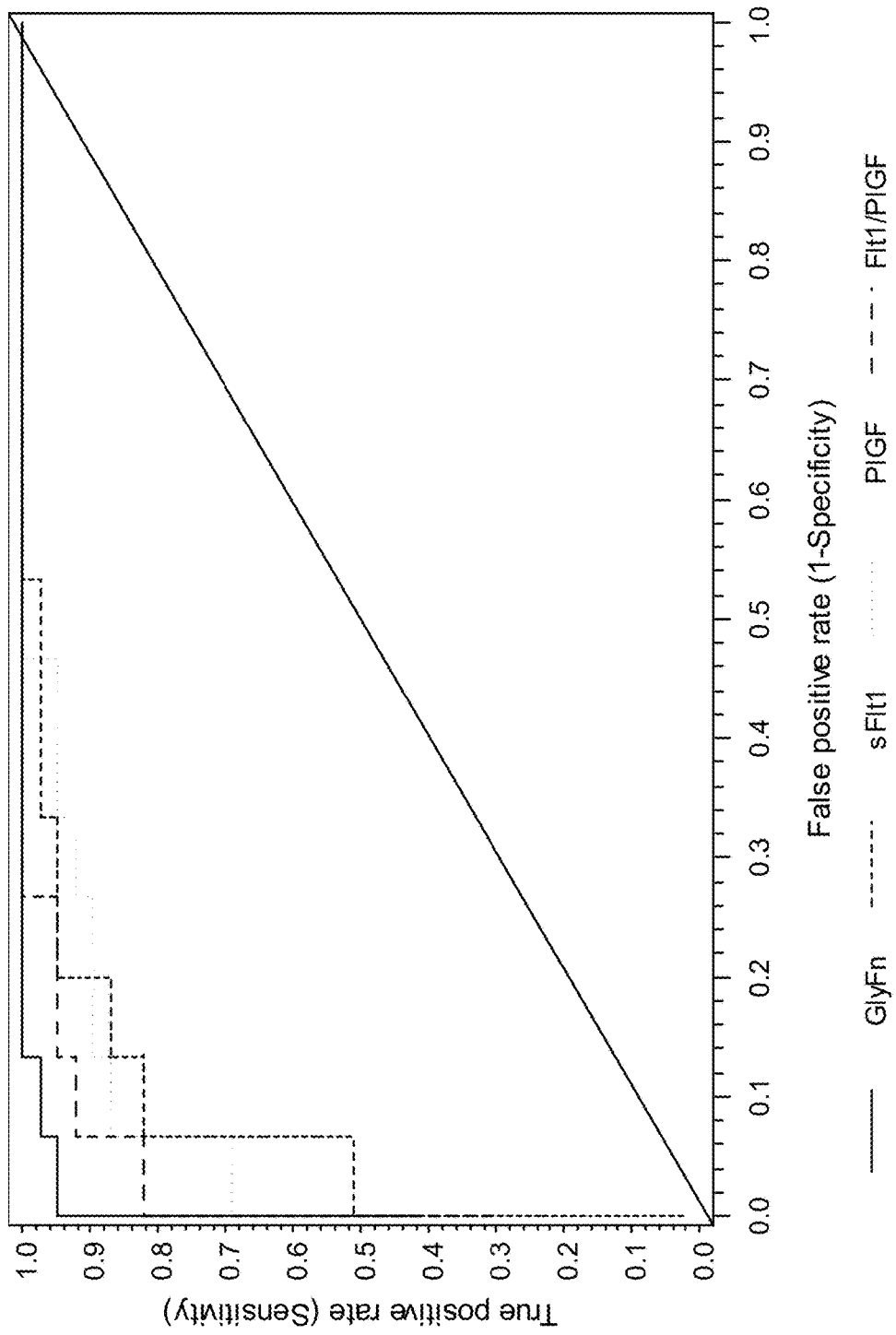

FIGS. 6A and 6B are a table showing average weekly change in GlyFn concentration by week and preeclampsia status (FIG. 6A), and a receiver operating characteristic curves showing third-trimester preeclampsia classification performance of biomarkers within all cohorts (FIG. 6B), in accordance with various embodimentsA repeated-measures analysis of change over time in biomarkers found that, in controls, there was not a significant change in GlyFn (p=0.83) across the span of pregnancy. In patients with preeclampsia, the weekly change between 33 and 38 weeks was 81.7 (SE 94.1) µg/ml for participants with mild preeclampsia and 195.2 (SE 88.2) µg/ml for participants with severe preeclampsia.

FIG. 7 is a table showing third-trimester preeclampsia classification performance of biomarkers within all cohorts, and FIG. 8 is a table showing GlyFn POC values for prediction of preeclampsia at varying prevalence estimates, in accordance with various embodiments. The clinical utility of these biomarkers for detection of preeclampsia was tested via ROC curves. The AUROCs for GlyFn, sFlt1, PlGF, and the sFlt1/PlGF ratio are show in FIG. 7. Since the sFlt1 assay requires significant serum quantities, this analysis was restricted to 15 control and 39 preeclampsia participants between 20 and 39 weeks of gestation with sufficient serum for sFlt1 analysis. The AUROC for GlyFn was 0.99, and trended toward being significantly different from the AUROC for sFlt1 (AUROC: 0.96, p=0.11) and PlGF (AUROC: 0.94, p=0.10). Upon categorization at a threshold of 176.4 µg/ml, GlyFn demonstrated a sensitivity of 0.97 (0.85 to 1.00) and a specificity of 0.93 (0.66 to 1.00). At this threshold, and with an estimated population prevalence of 5% for preeclampsia, the positive predictive and negative predictive values were 47% (95% CI: 23-72%) and 89% (95% CI: 80-98%), respectively (FIG. 8).

FIG. 9 is a table showing the relationship of third-trimester GlyFn levels to clinical characteristics and outcomes in normotensives and clinical preeclampsia, in accordance with various embodiments. Thus, the results of post-hoc analyses of maternal and fetal outcomes versus GlyFn are presented in FIG. 9. GlyFn values had a significant linear relationship with gestational age at delivery, birth weight, blood pressure, uric acid, and ALAT. For every 100-µg/ml increase in GlyFn, there was a predicted decrease in gestational age at delivery of 0.59 weeks (4 days) (p<0.01), a decrease in birth weight of 129.4 grams (p<0.01), an increase in systolic blood pressure of 1.39 mm/Hg (p=0.04), an increase in diastolic blood pressure of 1-14 mm/Hg (p=0.01), an increase in uric acid of 13.6 µmol/L (p<0.01), and an increase of ALAT of 5.88 U/L (p<0.01). GlyFn was not significantly related to gestational age of diagnosis of preeclampsia (p=0.27) or proteinuria (p=0.68).

For participants with preeclampsia, there was a significant relationship between having an infant that was small-for-gestational-age and having a GlyFn level ≥500 µg/ml. Of participants with preeclampsia who had a GlyFn level of <500 µg, 8% (1/32) had infants that were small-for-gestational-age, while for participants with preeclampsia who had GlyFn levels ≥500 µg/ml, 26% (6/24) were small-for-gestational-age (p=0.03). There was not a significant relationship between having high GlyFn levels and HELLP or placental insufficiency in patients with preeclampsia (p=0.13 and p=0.27, respectively); however, a higher percentage of women with GlyFn levels ≥500 µg/ml developed HELLP (26% versus 8%; p=0.13) and placental insufficiency (26% versus 12%; p=0.27).

Results from the GlyFn plate assay were compared with the GlyFn POC assay on a subset of the samples. There was a strong correlation (r=0.76, p<0.01) between the plate and POC assays. ROC curves were generated for the two methods separately, and the AUROCs were similar between the plate (AUROC=0.99, 95% CI: 0.99 to 1.00) and POC (AUROC 0.93, 95% CI 0.85 to 1.00) assays. ROC curves were generated to compare the ability to distinguish between mild and severe PE for POC and plate assay, and the POC outperformed the plate assay (AUROC=0.78 versus 0.68).

Example 5: GlyFn as a Biomarker for Preeclampsia

GlyFn is shown herein to be a powerful biomarker for preeclampsia, and as such, GlyFn may be used in various assessment and diagnostic methods, such as assessing the progression of preeclampsia over time based on elevated levels in first-trimester maternal serum, and monitoring the progressive increase throughout pregnancy in order to predict or diagnose preeclampsia in a subject. As disclosed herein, increasing GlyFn levels were correlated with important clinical characteristics and outcomes, including earlier delivery, decreases in birth weight, and increases in blood pressure, uric acid, and ALAT. GlyFn is a uniquely useful analyte to monitor preeclampsia, since GlyFn levels remain constant in controls throughout pregnancy. The best sensitivity and specificity for prediction of preeclampsia were found to be at a cutoff for GlyFn of 176.4 µg/ml.

Thus, in various embodiments, measurement of serum GlyFn levels may be used in methods for the management of preeclampsia, methods of prediction of poor clinical outcomes (low birth weight, HELLP, etc.), and methods of distinguishing between mild and severe preeclampsia.

The superior performance of this GlyFn fraction presumably reflects a strong involvement of GlyFn with the pathological processes that initiate preeclampsia. Without being bound by theory, this, in turn, may reflect the particular involvement in preeclampsia development of Fn splice variants or proteolytic fragments that exhibit unique glycosylation patterns. It is of interest that oxygen levels have recently been reported to regulate expression of the core-1 O-glycan Galβ1-3GalNac epitope in human placenta; thus, without being bound by theory, placental insufficiency may contribute to altered glycoprotein level in preeclampsia.

Without being bound by theory, the association of GlyFn with gestational diabetes as well as preeclampsia may be a consequence of the fact that both conditions are associated with inflammation and endothelial dysfunction. Thus, first-trimester inflammation and endothelial dysfunction related to disrupted spiral artery remodeling may be linked to increased levels of a specific form of glycosylated Fn. The distinct patterns of GlyFn abundance in in these two related conditions remains of interest (e.g., consistently elevated in all trimesters in gestational diabetes but a progressive increase during the course of preeclampsia), but it may indicate that the factors that trigger gestational diabetes are established early in pregnancy and remain at a constant level, while initiation and development of preeclampsia involves a continuous increase in the conditions that produce GlyFn.

The methods disclosed herein enable the use of GlyFn as a biomarker for monitoring the severity of preeclampsia, as well as the use of GlyFn for predicting the development of preeclampsia, particularly in a first or second trimester patient. sFlt1 and PlGF are currently used in investigational studies for the diagnosis of preeclampsia, but not for early prediction or monitoring of disease progression. The correlation found between GlyFn and clinical outcomes is important and unique, in that it establishes a method for predicting which patients will have poor maternal and/or fetal outcomes. This analysis showed that GlyFn is significantly different between patients with and without preeclampsia across the span of pregnancy (including before the clinical presentation of preeclampsia), which has not been shown for other preeclampsia analytes and supports the idea of an early pathogenesis of the disease. As disclosed herein, elevated GlyFn levels may serve as an early indicator of risk for preeclampsia.

The ability to use this test in a POC format provides a method for practitioners to quickly determine risk for preeclampsia in their pregnant patients and to determine risk for poor maternal and fetal outcomes among those patients with preeclampsia.

Example 6: Glycosylated Fibronectin Lateral Flow Immunoassay (FN LFIA)

In some embodiments, GlyFn levels may be assessed using a lateral flow device. Various lateral flow assay methods may be utilized to test for the presence or absence or quantity of an analyte, such as GlyFn, in a biological sample. In one example, a "sandwich" assay method uses an antibody immobilized on a solid support, which forms part of a complex with a labeled antibody, to determine the presence of a target analyte by observing the presence and amount of bound analyte-labeled antibody complex. For the purposes of a lateral flow immunoassay, the label may be an enzyme, colored microspheres, fluorescently-labeled microspheres, or may use other similar detection methods that provide for detection and/or quantification of analyte bound to the test line.

Conventional lateral flow test strips feature a solid support on which the sample receiving area and the target capture zones are supported. The solid support material is one which is capable of supporting the sample receiving area and target capture zones and providing for the capillary flow of sample out from the sample receiving area to the target capture zones when the lateral flow test strip is exposed to an appropriate solvent or buffer which acts as a carrier liquid for the sample. General classes of materials that may be used as support include organic or inorganic polymers, and natural and synthetic polymers. More specific examples of suitable solid supports include, without limitation, glass fiber, cellulose, nylon, crosslinked dextran, various chromatographic papers and nitrocellulose. One particularly useful material is nitrocellulose.

Figure 10A:
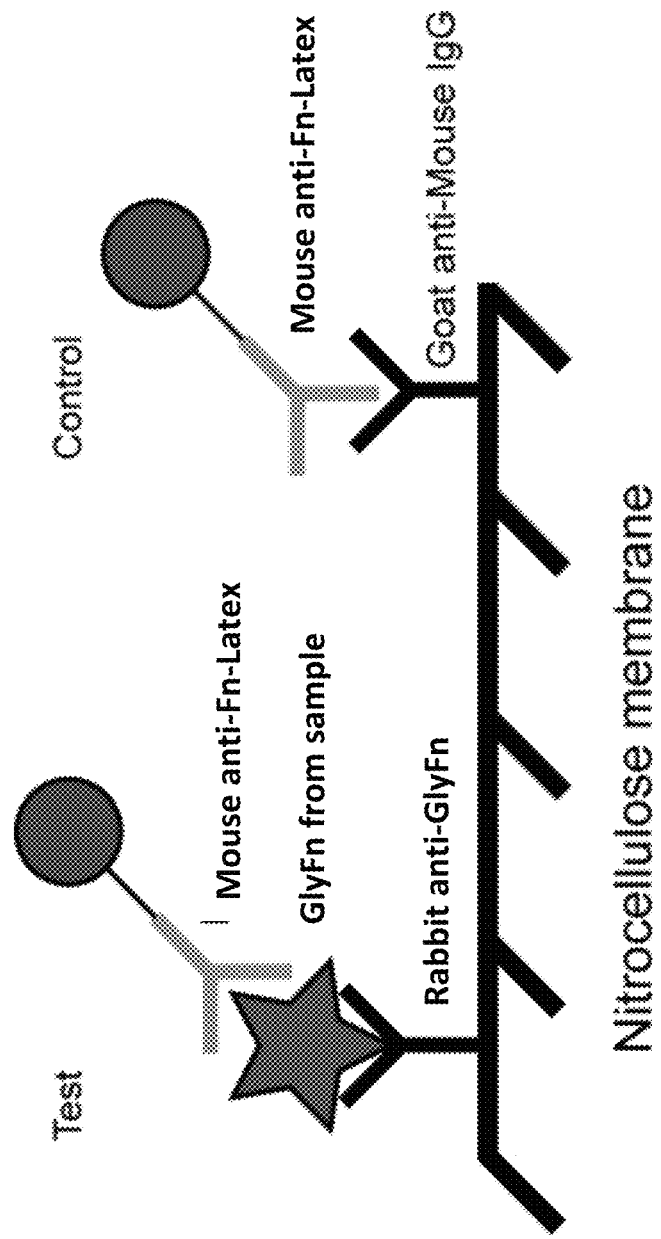
FIGS. 10A and 10B illustrate a schematic diagram showing an example of a lateral flow immunoassay (FIG. 10A) and a lateral flow test device (FIG. 10B) that may be used in accordance with various embodiments disclosed herein.
Figure 10B:
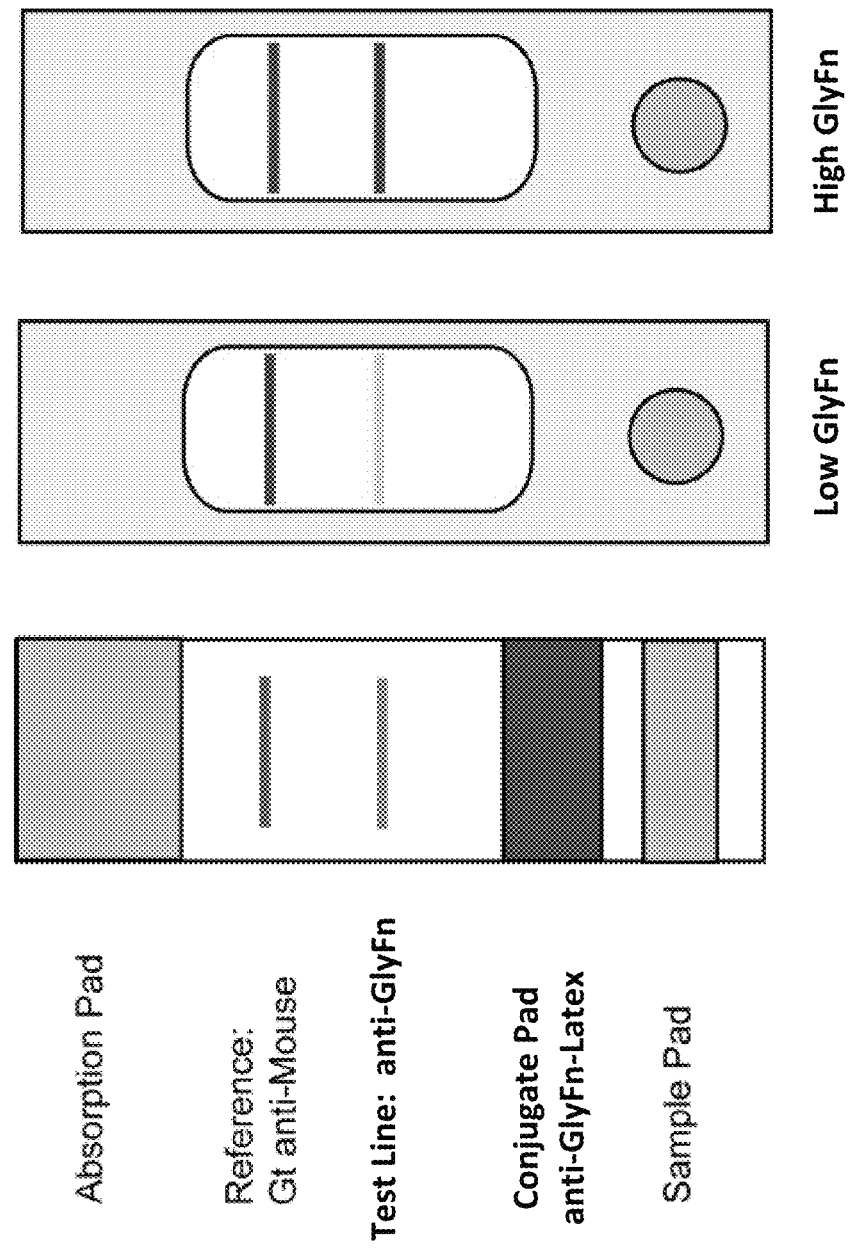

FIGS. 10A and 10B illustrate a schematic diagram showing an example of a lateral flow immunoassay (FIG. 10A) and a lateral flow test device (FIG. 10B) that may be used in accordance with various embodiments disclosed herein. In one specific, non-limiting example of such a device, 200 µg/mL Rabbit anti-GlyFn is immobilized on the membrane as a test line (0.5 µL/strip) and 300 µg/mL goat anti-mouse IgG is immobilized as the procedural control line (0.5 µL/strip). Mouse anti-Fn-conjugated microspheres (10 µL of 150 µg/mL mouse anti-fibronectin, 1 mg/mL solids) are dried onto a conjugate pad that has been treated with a solution containing (per liter): 3.81 g sodium borate, 2.0 g dextran, 5.0 g BSA, 1.0 g Tween-20, and 0.5 g sodium azide, pH 8.0, followed by drying for 1 hour at 50° C.

The sample is then diluted 1:500 in HEPES Running Buffer (10 mM HEPES, 0.1 mM $CaCl_2$, 155 mM NaCl, 0.1% $NaN_3$, 0.75% Tween-20, and 0.01% polyvinyl alcohol). When a sample is applied to the sample pad, capillary flow allows the GlyFn-containing sample to hydrate and interact with the labeled microspheres, forming GlyFn-labeled microsphere complexes, which further migrate to the test line, where they are captured by the rabbit anti-GlyFn.

Following completion of the capillary migration, the device is scanned, and the amount of GlyFn in the sample is determined by quantitative densitometry relative to a standard curve using purified GlyFn as a standard. Although a particular lateral flow device is described herein, one of skill in the art will appreciate that lateral flow devices are conventional, and that variations of the disclosed device may be used.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method, comprising:
   obtaining a maternal serum sample from a subject at 30 or more weeks of pregnancy;
   providing a lateral flow device, comprising
     a housing; and
     a test strip contained within the housing, the test strip comprising one or more immunoreagents, wherein one of the one or more immunoreagents is an antibody which binds to fibronectin glycosylation associated with *Sambucus nigra* lectin binding (anti-GlyFn antibody);
   applying the maternal serum sample to the test strip under conditions sufficient for fibronectin glycosylation associated with *Sambucus nigra* lectin binding (Fn-SNA) in the maternal serum to be captured by the anti-GlyFn antibody and form a Fn-SNA-anti-GlyFn antibody complex;
   determining, via the lateral flow device, a level of Fn-SNA-anti-GlyFn antibody complex corresponding to at least 175 µg/ml Fn-SNA in the maternal sample, wherein the determining includes scanning the lateral flow device and quantifying the level of Fn-SNA-anti-GlyFn antibody complex by quantitative densitometry of a test line to which the Fn-SNA-anti-GlyFn antibody complex is bound; and
   managing preeclampsia associated with the subject.

2. The method of claim 1, wherein managing preeclampsia further comprises:
   preparing the subject for delivery where the level of Fn-SNA-anti-GlyFn antibody complex corresponds to greater than 175 µg/ml Fn-SNA in the maternal sample.

3. The method of claim 1, wherein the method further includes selecting the subject, wherein the subject is at risk for preeclampsia prior to obtaining the maternal serum sample.

4. The method of claim 1, wherein managing preeclampsia further comprises:

preparing the subject for delivery, wherein the level of Fn-SNA-anti-GlyFn antibody complex corresponds to 176.4 μg/ml or higher Fn-SNA in the maternal sample.

5. The method of claim 1, wherein managing preeclampsia further comprises:

preparing the subject for delivery, wherein the level of Fn-SNA-anti-GlyFn antibody complex corresponds to 200 μg/ml or higher Fn-SNA in the maternal sample.

6. The method of claim 1, wherein managing preeclampsia further comprises:

preparing the subject for delivery, wherein the level of Fn-SNA-anti-GlyFn antibody complex corresponds to greater than 250 μg/ml Fn-SNA in the maternal sample, indicating that the subject has severe preeclampsia.

7. The method of claim 1, wherein the method further comprises determining whether the measured level of FN-SNA is equal to or greater than 250 μg/ml, wherein a measured level of FN-SNA equal to or greater than 250 μg/ml indicates that the subject is at risk of low birth weight or HELLP syndrome.

8. The method of claim 1, wherein the method further comprises determining whether the measured level of FN-SNA is equal to or greater than 500 μg/ml, wherein a measured level of FN-SNA equal to or greater than 500 μg/ml indicates that the subject is at high risk of low birth weight or HELLP syndrome.

9. The method of claim 1, wherein managing preeclampsia further comprises performing a subsequent test of the level of Fn-SNA-anti-GlyFn antibody complex at a later time on a second maternal serum sample via the lateral flow device, wherein the level of Fn-SNA-anti-GlyFn antibody complex corresponds to greater than 175 μg/ml Fn-SNA in the subsequent test of the second maternal serum sample.

10. The method of claim 1, wherein managing preeclampsia further comprises performing a subsequent test of the level of Fn-SNA-anti-GlyFn antibody complex at a later time on a second maternal serum sample via the lateral flow device, wherein the level of Fn-SNA-anti-GlyFn antibody complex corresponds to 176.4 μg/ml or higher Fn-SNA in the subsequent test of the second maternal serum sample.

11. The method of claim 1, wherein managing preeclampsia further comprises performing a subsequent test of the level of Fn-SNA-anti-GlyFn antibody complex at a later time on a second maternal serum sample via the lateral flow device, wherein the level of Fn-SNA-anti-GlyFn antibody complex corresponds to 200 μg/ml or higher Fn-SNA in the subsequent test of the second maternal serum sample.

12. The method of claim 1, wherein managing preeclampsia further comprises performing a subsequent test of the level of Fn-SNA-anti-GlyFn antibody complex at a later time on a second maternal serum sample via the lateral flow device, wherein the level of Fn-SNA-anti-GlyFn antibody complex corresponds to greater than 250 μg/ml Fn-SNA in the maternal sample, indicating that the subject has severe preeclampsia.

* * * * *